US006456872B1

(12) United States Patent
Faisandier

(10) Patent No.: US 6,456,872 B1
(45) Date of Patent: Sep. 24, 2002

(54) HOLTER-TYPE APPARATUS FOR RECORDING PHYSIOLOGICAL SIGNALS INDICATIVE OF CARDIAC ACTIVITY

(75) Inventor: Yves Faisandier, Montrouge (FR)

(73) Assignee: Ela Medical S.A., Montrouge (FR)

( * ) Notice: Subject to any disclaimer, the term of this patent is extended or adjusted under 35 U.S.C. 154(b) by 25 days.

(21) Appl. No.: 09/603,724

(22) Filed: Jun. 23, 2000

(30) Foreign Application Priority Data

Jun. 23, 1999 (FR) .............................................. 99 08028

(51) Int. Cl.$^7$ ............................................. A61B 5/0432
(52) U.S. Cl. ........................ 600/523; 600/390; 600/393
(58) Field of Search ................................. 600/393, 390, 600/382, 509, 520, 523, 524

(56) References Cited

U.S. PATENT DOCUMENTS

| 3,943,918 A | | 3/1976 | Lewis ...................... 128/2.1 A |
| 4,181,134 A | | 1/1980 | Mason et al. ................ 128/689 |
| 4,635,646 A | | 1/1987 | Gilles et al. ................ 128/696 |
| 4,889,131 A | * | 12/1989 | Salem |
| 5,016,636 A | * | 5/1991 | Kulakowski |
| 5,443,494 A | * | 8/1995 | Paolizzi |
| 5,445,149 A | * | 8/1995 | Rotolo |
| 5,511,553 A | * | 4/1996 | Segalowitz |
| 6,065,154 A | * | 5/2000 | Hulings |
| 6,117,077 A | * | 9/2000 | Del Mar ...................... 600/301 |

FOREIGN PATENT DOCUMENTS

| EP | 0 284 943 A | 10/1988 |
| FR | 2 554 704 | 5/1985 |
| FR | 2 748 928 | 11/1997 |

\* cited by examiner

*Primary Examiner*—George R. Evanisko
*Assistant Examiner*—Roderick Bradford
(74) *Attorney, Agent, or Firm*—Orrick, Herrington & Sutcliffe LLP

(57) ABSTRACT

A Holter-type apparatus for the recording of physiological signals indicative of cardiac activity. This apparatus has a base unit formed of a flexible sheet carrying the electrodes collecting the physiological signals and the conductive connection elements connected to the electrodes. The base unit has a central area receiving a recording case and which contains contact areas forming the proximal terminations of the respective conductive connection elements. The recording case is equipped to be fastened to the base unit central area and to have electrode contacts that make electrical contact with contact areas of the base unit. The base unit also can carry a battery to supply power to the recording case. The base unit is advantageously made of a sheet of flexible printed circuit material carrying a conducting pattern forming the aforementioned electrodes, conductive connection elements and contact areas.

10 Claims, 2 Drawing Sheets

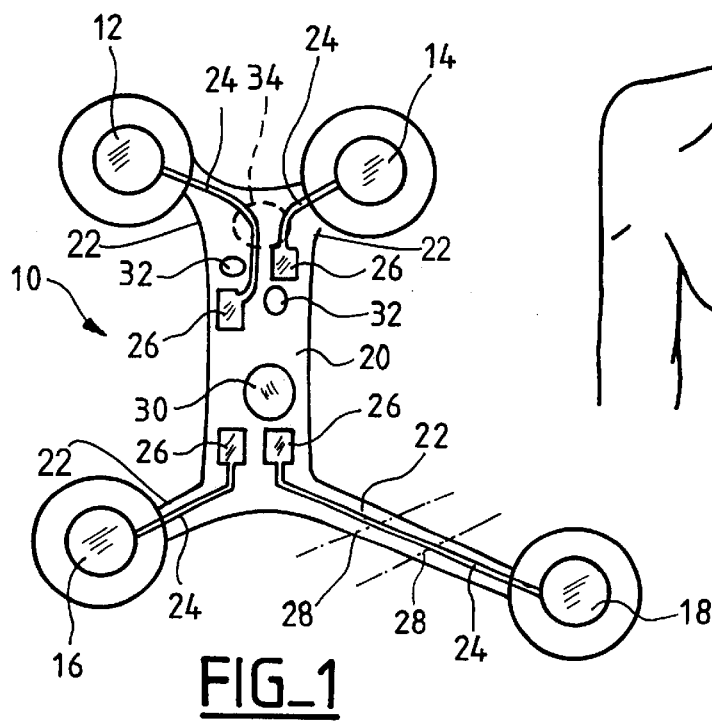
FIG_1
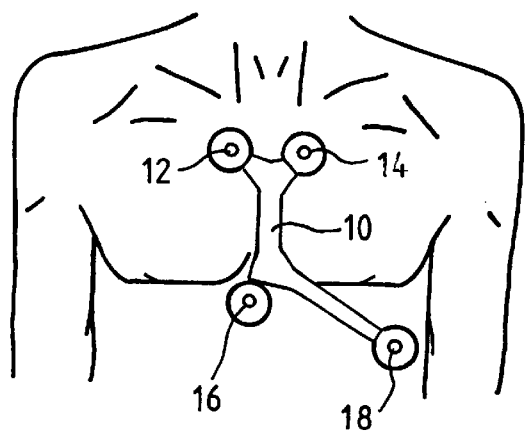
FIG_2
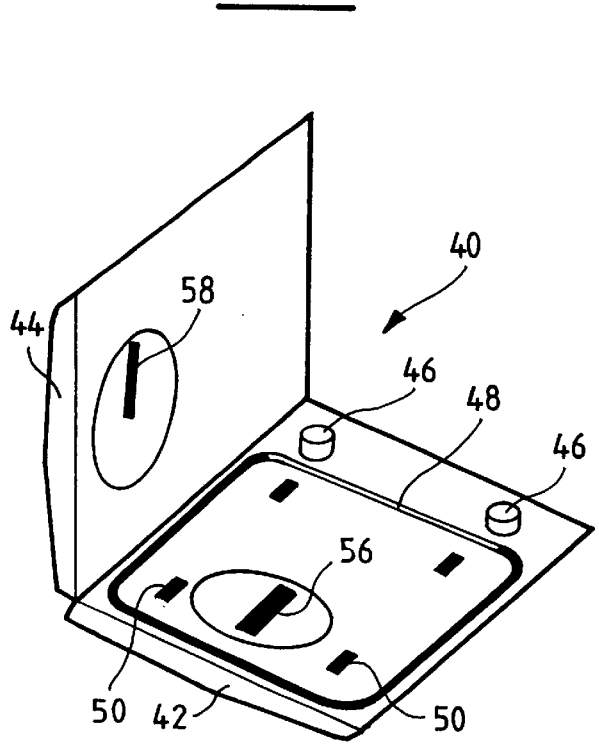
FIG_3
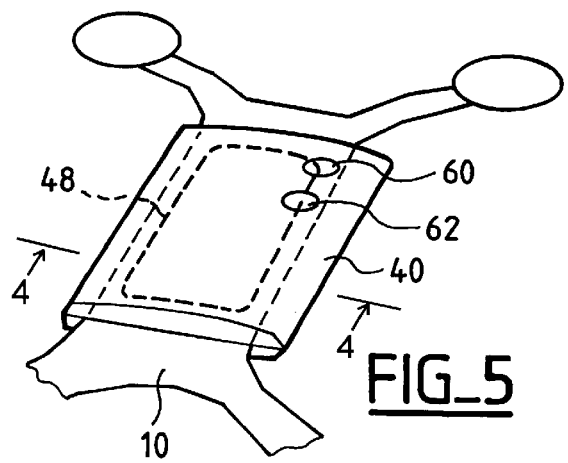
FIG_5
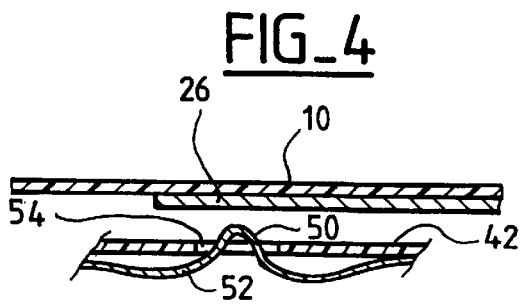
FIG_4

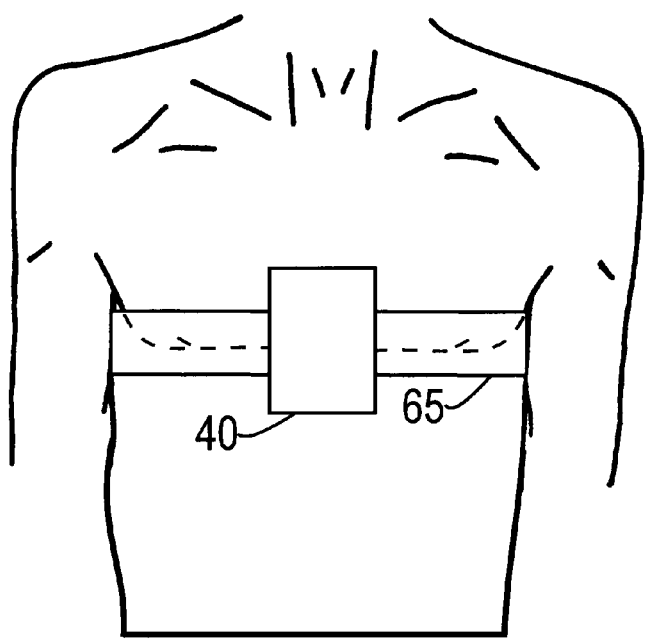
FIG_6
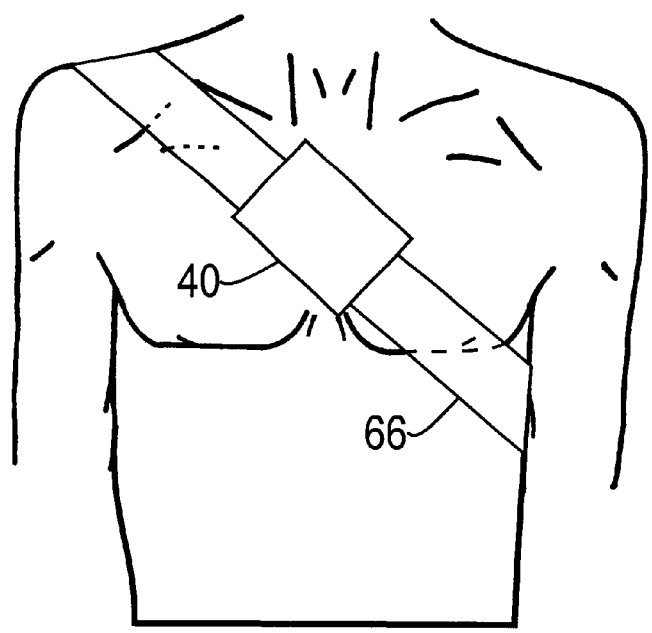
FIG_7

HOLTER-TYPE APPARATUS FOR RECORDING PHYSIOLOGICAL SIGNALS INDICATIVE OF CARDIAC ACTIVITY

FIELD OF THE INVENTION

The present invention relates to a "Holter"-type apparatus for recording physiological signals indicative of a patient's cardiac activity, which signals are collected (i.e., sensed) by external electrodes applied to the patient, and more particularly to a portable Holter-type apparatus intended to provide uninterrupted, long-term, ambulatory recording of cardiac activity signals.

BACKGROUND OF THE INVENTION

Holter recording devices are known which traditionally use an analog or digital recording technique. These devices typically have either a magnetic cassette tape or a static digital memory, and batteries, which are disposed in a case. Cables are used to connect the case to the electrodes which are coupled to the patient for collecting the signals to be recorded.

The case is then worn by the patient, either over the shoulder as a shoulder-belt-type harness or attached to a belt around the waist or other body part of the patient.

A major disadvantage of these known Holter devices arises from the discomfort to and inconvenience suffered by the patient because of the interference caused by the cables, for example, when bathing, taking a shower, changing clothes. In such cases, the cables can become ensnarled in the patient's clothing or movements, and the apparatus can become dislodged and quite possibly may fall to the ground. In addition, as the patient must remain in close physical proximity to the apparatus when used during sleeping, he or she runs the risk of turning over and crushing the apparatus or accidentally ripping the cables out of their sockets, for example, when getting up. Further, certain types of clothing, and in particular women's clothing, do not allow for easy passage of the cables between the thorax and the electrodes on the recorder case, particularly when the recorder is worn in an over-the-shoulder position.

OBJECTS AND SUMMARY OF THE INVENTION

It is, therefore, an object of the present invention to remedy the disadvantages described above by proposing a new Holter apparatus structure, which is particularly compact and which additionally minimizes a patient's discomfort.

Broadly, the present invention is directed to a Holter system having a "sole" or "base" unit, which incorporates the electrodes and their respective electric connections, and a recording case affixed directly to the base unit. Thus, the recording case, instead of being fastened to a belt or carried over-the-shoulder in a shoulder belt and connected by cables to the patient, will be supported directly by the base unit, eliminating the need for cables and the problems caused by the cables. The interconnected case and base unit thus provide a "wireless" Holter recording device which is supported by electrodes on the patient.

In a preferred embodiment, the invention is directed towards an apparatus, including a base unit, that is formed of a flexible sheet carrying electrodes and conductive connection elements. The base unit has a central area for receiving a recording case, which attaches to the base unit. The base unit central area also is equipped with contact areas which are the proximal terminations of the respective conductive connection elements. In this embodiment, the recording case has a means for attaching to the central area of the base unit, and electrode contacts which are configured to make the appropriate electrical contacts with the proximal termination areas of base unit conductive connection elements.

In one embodiment, the central area of the base unit forms a thoracic belt or strap, which serves as the support for the recording case. In other words, the recording case means for attaching structure functions to attach the recording case to the thoracic belt of the base. Preferably, the base unit also carries a battery to supply power to the recording to the recording case.

The base unit is preferably made of a sheet of flexible printed circuit material on which is etched or engraved a conductive pattern forming the aforementioned electrodes, contact areas and conductive connection elements connecting the electrodes to their respective contact areas.

The recording case is preferably a two-piece structure having a base and a cover that, when closed, secures the recorder base firmly to the base unit in electrical contact. More preferably, the recorder case and cover have a hinge, even more particularly an articulated hinge, along a common side. Advantageously, the recording case also comprises a peripheral seal surrounding at least the aforementioned electrode contact areas and, if necessary, the battery contact points of the base unit, so as to provide fluid resistance for the electrical connections.

The recording case and the base also preferably comprise cooperating structures for respectively centering and supporting the assembly. For example, protruding studs and cooperating holes or detents respectively mounted on the base unit and recording case, or vice versa, or in different combinations, may be used to position the recording case securely to the base unit in the proper orientation and without relative movement there-between.

BRIEF DESCRIPTION OF THE DRAWINGS

Further features, characteristics, and advantages of the present invention will become apparent to a person of ordinary skill in the art in view of the following detailed discussion of a preferred embodiment of the invention, which is described with reference to the attached drawings, in which like reference characters refer to like elements, and in which:

FIG. 1 shows a plan view of the base unit with electrodes;

FIG. 2 shows the base unit of FIG. 1 placed upon the thorax of a patient before the recording case is affixed thereto;

FIG. 3 is an elevated perspective of the recording case in an open position;

FIG. 4 shows a partial cross sectional view taken along line 4—4 of FIG. 5; and

FIG. 5 is a perspective view of the recording case in a closed position about the base unit.

FIG. 6 shows the base unit of FIG. 1 carried by a thoracic belt.

FIG. 7 shows the base unit of FIG. 1 carried by a hanging strap collar.

DETAILED DESCRIPTION OF THE INVENTION

As previously noted, the invention is directed to a self-supporting Holter apparatus, having two distinct elements, namely, a "sole" or "base" unit comprising the electrodes, on the one hand, and the recording case which is affixed to the base, on the other hand.

On FIGS. 1 and 2, reference 10 indicates, in a general way, the base unit, which is a monobloc element or single integrated structure carrying a plurality of electrodes, e.g., four electrodes, namely, two electrodes 12, 14 at the top and two electrodes 16, 18 at the bottom, used for acquiring the electrical signals indicative of cardiac activity. These electrodes are of a known type and are conventionally affixed on the thorax (FIG. 2) either through adhesion or through depression using suction cups.

Base unit 10 is advantageously constructed as a flexible printed circuit that can be cut to a desired shape, and onto which the electrodes are deposited. The electrodes may be formed by depositing a fine Ag-AgCl layer onto the metal of the printed circuit to ensure optimal interfacing with the skin. Disposed around the electrode is an adhesive ring and a contact gel, or a conducting adhesive, to ensure the necessary electrical and mechanical qualities for the collection of the electrocardiograph signal.

Alternatively, it is also possible to envisage mounting electrodes and/or conductive connection elements onto the flexible circuit, provided that the base unit constitutes a unitary, monobloc element.

It is also possible to envisage using electrodes which are known as "active" electrodes, i.e., electrodes which have a preamplifier (an emitter-following amplifier) integrated into the electrode. This technique allows for producing at the electrode output a voltage signal level which is relatively high that in particular, makes it possible to work without the need for applying a conducting gel to the skin.

It should be noted, however, that because the conductive connection elements of the base unit, which connect each electrode to its respective contact area which, in turn, is connected to a recorder case input, have a length that is minimized, and is much shorter than that of the cables connecting the prior art Holter devices to the electrodes, the level of noise appearing in the device of the present invention will be, in any case, lower than the level of noise found in a traditional Holter apparatus. This noise reduction occurs whether the invention is used with the aforementioned active electrodes or with simple passive electrodes.

Base unit 10 comprises a lengthened central area 20 (FIG. 1) whose two ends are prolonged by extension arms 22, which contain the electrodes 12, 14, 16 and 18 and conductive wires or traces forming conductors 24, i.e., the conductive connection elements, to the respective electrodes. Each conductor 24 is electrically connected to an electrode at its distal end, and ends in a contact area 26 at its proximal end located on central area 20. The contact areas 26 (also known as contact pads) for the various electrodes 12, 14, 16 and 18 are thus gathered on central area 20.

The position of the electrodes, i.e., the general configuration of the length and the orientation of the extension arms 22, preferably corresponds to known standards for Holter recording, with a good separation of the derivation axes.

The flexible printed circuit of base unit 10 is typically an inextensible structure, and thus it is not possible to adapt spontaneously the dimensions of base unit 10 to fit all sizes of patients. Therefore, base unit 10 is provided with either a system of folds 28 (FIG. 2) (which can be folded or unfolded to adjust the size of base unit 10 to fit the patient) or of complex forms, or, alternatively or additionally, base unit 10 is provided in models of several different sizes which must be envisaged or the most distant electrodes. Moreover, central area 20, on which the recorder case 40 is fixed in position, must allow for a maximum of comfort to the patient, an excellent secure connection to the recorder case 40, and a minimum distance between the electrodes 12, 14, 16 and 18 and the contact areas 26 in order to minimize any interference and noise.

The conductive connection elements 24 between the electrodes and the contact areas are electrically isolated from the patient, preferably using a layer of varnish compatible with the constraints imposed by direct contact with the human body. At the place of contact area 26, the copper of the printed circuit is preferably covered (plated) with nickel deposit or a very fine layer of gold to ensure an effective protection against oxidation.

Base unit 10 can comprise a power supply battery 30 for the recording case 40 that will be placed on the base unit 10, or a large capacitor, e.g., 1 farad (not shown) for storing energy.

Base unit 10 also may be equipped with a plurality of holes 32 which are used for mechanically positioning recording case 40, as will be explained in more detail below.

Base unit 10 thus set up is considered as a disposable or "single use" item to be changed with each examination, i.e., a Holter recording of electrocardiograph (EKG) signals over a set time, as previously had been the case with the prior known Holter devices, on the one hand, for the set of electrodes, and, on the other hand, for the recording case batteries. Because the base unit 10 can incorporate the battery, this advantageously simplifies preparing the system to take another holter recording of physiological signals (EKG) because now only the base unit 10 needs to be changed.

The base also can be equipped with a shielding along the conductive traces to the electrodes, as well as a fifth electrode 34 coupled to ground (FIG. 1), which can be incidentally used as a fastener to support the base unit 10 on the thorax. Indeed, it is advisable not to pull upon an electrode wire which can cause movement between the metal conductive surfaces and the skin and which could create spurious or parasitic voltages appearing in the EKG recording. Ground electrode 34 thus can be used to minimize such movement of base unit 10. As illustrated in FIG. 1, while placing ground electrode 34 at the assemblage point near the two upper electrodes 12, 14, ground electrode 34 can then support the weight of the apparatus, and the conductors 24 with the signal collection electrodes 12, 14, 16 and 18 can remain mechanically floating.

Alternatively, it is possible to provide the mechanical stabilizing function with a simple passive adhesive, e.g., an adhesive patch, without using a ground electrode, if a ground electrode is not necessary to obtain good electric performance.

FIG. 3 shows the recording case 40, intended to cooperate with base unit 10. Recording case 40, which is to be connected to base unit 10, is supported by the base unit 10. Recording case 40 preferably comprises a grip-connector that either surrounds the base unit 10, as in the illustrated example, or alternatively includes a connection mechanism that fastens it securely to base unit 10.

In the case of a base unit 10 made of a flexible printed circuit, recorder case 40 can, in particular, be produced in the illustrated form of FIG. 3, with a lower part or base 42 and a cover 44 which are connected by an articulated hinge allowing the cover 44 to fold back over 42 to close around the base unit 10, gripping securely base unit 10 in its central part 20 without crushing base unit 10, as illustrated on FIG. 5.

The precise positioning of base 42 relative to base unit 10 is ensured by the use of protruding centering and support elements 46, which cooperate with holes 32 of base unit 10 to fit therein and secure the elements together. It should be understood that other mechanical positioning and support structures could be used, such as notches placed at the periphery of recording case 40, which correspond to the periphery of base unit 10 to position recording case 40 or base unit 10 in the correct position and orientation and hold them fixed in place.

A seal 48 surrounding the portion of base unit 10 containing the contact areas 26 is additionally envisaged. When the recording case is closed, the peripheral seal 48 is forced against the printed circuit area of base unit 10, thus preventing any introduction of liquid (body fluids, water, etc.) into the region of the contact areas 26. It is also possible to place one or more additional seals on cover 44 to ensure the sealing of any possible contact point, e.g., with an upper battery contact 58 (see below).

Base 42 of recording case 40 is equipped with contacts 50 which are positioned to make contact with contact areas 26 of the base unit 10. These contacts 50 are implemented, for example, as illustrated on FIG. 4, by means of an elastically deformable "flat" spring 52 emerging from an opening 54 of base 42, so as to come in elastic contact against contact area 26 of base unit 10. Preferably, contacts 50 are laid out on base 42 of the recording case 40 in order to use, for the manufacture of the base unit 10, only one single-face printed circuit.

The base 42 also comprise a contact electrode 56 for contacting one of the poles of battery 30 in base unit 10. If battery 30 is a button-style battery, i.e., the positive and negative poles are respectively located on the front and back of the printed circuit of base unit 10, it may be necessary to provide on cover 44 a contact 58 which is connected to the other pole of the button battery 30, for simplicity of construction of base unit 10. In the case of a flat battery 30, and even with button batteries, it is possible and preferable to locate all the battery contacts of both base unit 10 and case 40 on the same side, respectively, and therefore to group the battery contacts 56 and 58 on base 42 with the other contacts 50 in a cooperating position.

The recording case 40 comprises electronic circuits for the collection and processing of the EKG signals, which are of and in themselves traditional and known. Since they do not form a part of the present invention, they will not be described more in detail. However, suitable electronic circuits are, for example, those comparable with those of the Syneflash model Holter device, which is available from ELA Médical S.A.

The electronic circuits are, however, advantageously grouped in base 42 of the recording case 40. If one wishes to minimize the connections between base 42 and cover 44, and if all the contact areas are located on the base 42, then the cover 44 can be simply a plastic part.

During the close of the cover 44 and base 42, the recorder case 40 can be energized, either by making contact with battery 30 or by an additional mechanical or electronic switch. A mechanical bolt or clasp (not shown) can be used to secure the closing of the apparatus and to prevent inadvertent energizing.

Once the recording case 40 is closed about base unit 10, as illustrated in FIG. 5, a luminous and/or sound actuator 60 makes it possible to check the correct operation of the system. A window 62 for an infrared data transmission port, for example, of the IrdA type, may be provided for the bi-directional exchange of data, control parameters and information between the processor of the Holter recorder and the remote system associated with programming and exploitation of the data.

Various alternative implementations can be considered and employed. Thus, instead of providing battery 30 on base unit 10, it is possible to place battery 30 inside the recording case 40. This embodiment is particularly advantageous for electronics having an extremely reduced power consumption, in which case a simple "button" battery of a few grams can supply the case 40 with power during several months of use. In such a case, it is not necessary to change the battery with each examination, and thus not useful to integrate battery 30 in base unit 10. It is, however, advantageous to include also a battery voltage-inspecting device or low-battery power detector in order to alert the user when the battery is depleted and a replacement is needed.

In the example described above, the recording case 40 is entirely supported by the base unit 10 which thus allows for, inter alia, a means of support of the case. This characteristic, however, is not essential and it is possible that the case 40 not be carried by the base unit 10, but that it instead may be carried by a thoracic belt 65, such as that used by cardio-frequency monitors for sportsmen and athletes. Alternatively, case 40 may be supported by a collar 66, such as that used in a hanging strap style of device. Because these case 40 support mechanisms result in substantially reduced mechanical forces exerted on the interface between the base unit 10 and the patient's skin, it is then possible not to use adhesives to support and secure the electrodes 12, 14, 16 and 18 to the patient. These electrodes instead can be fixed, for example, by a depression-based system, with the energy of depression coming from the case 40 itself. The absence of an adhesive is particularly desirable in those instances where the device of the invention is to be used by sportsmen, or by patients prone to heavy perspiration or coetaneous allergies.

One skilled in art will appreciate that the present invention can be practiced by other than the described embodiments, which are presented for purposes of illustration and not of limitation.

I claim:

1. An apparatus for Holter-type recording of physiological signals corresponding to cardiac activity collected by external electrodes applied to a patient, comprising a set of electrodes, a recording case, and conductive connection elements for electrically connecting electrodes to the case, and a base unit formed of a flexible sheet carrying the electrodes and the conductive connection elements, said base comprising a central area for receiving the recording case and a plurality of contact areas forming proximal terminations of the respective conductive connection elements, wherein the recording case further comprises a set of electrode contacts and means for fixing the recording case to the base unit central area, said electrode contacts being disposed to make electrical contact with said base unit contact areas, respectively, when said recording case is fixed to said base unit, and wherein said recording case further comprises a base and a cover connected together along a common side, said base and cover having an open position and a closed position, wherein in said closed position, the base and cover grip the base unit central area to fix the recording case thereto.

2. The apparatus of claim 1, wherein the base unit central area comprises a support for the recording case.

3. The apparatus of claim 1, further comprising a thoracic belt coupled to the recording case to support the recording case against the base unit.

4. The apparatus of claim 1, further comprising a hanging strap coupled to the recording case to support the recording case against the base unit.

5. The apparatus of claim 1, wherein the base unit further comprises a battery power supply and wherein the recording case further comprises battery contacts to draw power from said battery.

6. The apparatus of claim 5, further comprising a peripheral seal disposed around said battery contacts.

7. The apparatus of claim 1, wherein the base further comprises a sheet of flexible printed circuit material, wherein said electrodes, the conductive connection elements and the contact areas further comprise a conductive pattern formed on said printed circuit.

8. The apparatus of claim 1, wherein the recording case further comprises a peripheral seal disposed around said surrounding electrode contracts.

9. The apparatus of claim 1, wherein the recording case and the base unit further comprise respective cooperating means for mutual centering and support of the recording case and the base unit.

10. The apparatus of claim 9, wherein the respective cooperating means for mutual centering and support further comprise protruding studs cooperating with corresponding holes.

* * * * *

UNITED STATES PATENT AND TRADEMARK OFFICE
CERTIFICATE OF CORRECTION

PATENT NO. : 6,456,872 B1
DATED : September 24, 2002
INVENTOR(S) : Yves Fraisandier It is certified that error appears in the above-identified patent and that said Letters Patent is hereby corrected as shown below:

Column 2,
Lines 55, and 57, respectively after "5;" delete "and"; and after "unit." delete "." and insert -- ; --;
Line 13, after "power" delete "to the recording"
Line 59, after "belt" delete "." and insert -- ; and --;

Column 3,
Line 31, after "that" insert -- , --;
Line 67, change "or" to -- for --

Column 4,
Line 29, after "another" delete "holter" and insert -- Holter --;

Column 5,
Line 30, after "42 also" delete "comprise" and insert -- comprises --;

Column 8,
Line 3, delete "contracts" and insert -- contacts --.

Signed and Sealed this

Twenty-eighth Day of December, 2004

JON W. DUDAS
*Director of the United States Patent and Trademark Office*